United States Patent [19]

Zhang et al.

[11] Patent Number: 5,695,781
[45] Date of Patent: Dec. 9, 1997

[54] SUSTAINED RELEASE FORMULATION CONTAINING THREE DIFFERENT TYPES OF POLYMERS

[75] Inventors: Guohua Zhang, Parsippany; Prasad Pinnamaraju, Edison, both of N.J.

[73] Assignee: Hallmark Pharmaceuticals, Inc., Somerset, N.J.

[21] Appl. No.: 395,565

[22] Filed: Mar. 1, 1995

[51] Int. Cl.$^6$ ............................................. A61K 9/22
[52] U.S. Cl. ........................... 424/468; 424/469; 424/486; 424/487; 424/488; 514/772.3; 514/779; 514/781; 514/960; 514/961
[58] Field of Search ........................... 424/464, 465, 424/469, 486, 488, 468, 487

[56] References Cited

U.S. PATENT DOCUMENTS

| | | | |
|---|---|---|---|
| 3,261,859 | 7/1966 | Dengel | 260/465 |
| 4,157,394 | 6/1979 | Fleckenstein et al. | 424/251 |
| 4,461,759 | 7/1984 | Dunn | 424/19 |
| 4,654,372 | 3/1987 | Marcoux | 514/646 |
| 4,697,035 | 9/1987 | Kisielowski et al. | 558/344 |
| 4,708,874 | 11/1987 | De Haan et al. | 424/470 |
| 4,753,802 | 6/1988 | Stephens et al. | 424/467 |
| 4,792,452 | 12/1988 | Howard et al. | 424/475 |
| 4,798,811 | 1/1989 | Lehmann et al. | 514/159 |
| 4,800,081 | 1/1989 | Albrecht et al. | 424/129 |
| 4,832,958 | 5/1989 | Baudier et al. | 424/473 |
| 4,859,469 | 8/1989 | Baudier et al. | 424/462 |
| 4,863,742 | 9/1989 | Panoz et al. | 424/473 |
| 4,952,672 | 8/1990 | Gremm et al. | 424/451 |
| 4,981,871 | 1/1991 | Abelson | 514/523 |
| 5,047,235 | 9/1991 | Lossnitzer et al. | 424/80 |
| 5,089,502 | 2/1992 | Sudilovsky et al. | 514/274 |
| 5,128,142 | 7/1992 | Mulligan et al. | 424/457 |
| 5,132,119 | 7/1992 | Lee | 424/646 |
| 5,132,295 | 7/1992 | Balz et al. | 514/54 |
| 5,169,639 | 12/1992 | Baichwal et al. | 424/468 |
| 5,230,901 | 7/1993 | Einig et al. | 424/468 |
| 5,252,337 | 10/1993 | Powell | 424/456 |
| 5,350,771 | 9/1994 | Pang et al. | 514/643 |

FOREIGN PATENT DOCUMENTS 1184497  3/1985  Canada.

Primary Examiner—James M. Spear
Attorney, Agent, or Firm—Staas & Halsey

[57] ABSTRACT

Verapamil depot drug formulations include the pharmaceutical itself and a three component release rate controlling matrix composition. The three components of the matrix composition are (1) an alginate component, such as sodium alginate, (2) an enteric polymer component, such as methacrylic acid copolymer, and (3) a pH independent gelling polymer, such as hydroxypropyl methylcellulose or polyethyleneoxide. The drug release rate can be adjusted by changing the amount of one or more of these components of the composition.

16 Claims, No Drawings

SUSTAINED RELEASE FORMULATION CONTAINING THREE DIFFERENT TYPES OF POLYMERS

FIELD OF THE INVENTION

The present invention is directed to formulations for preparing sustained release drug forms useful for releasing pharmaceuticals at controlled rates, generally in the stomachs and/or gastrointestinal tracts of hosts. In particular the invention relates to an improved depot drug form useful in connection with preparing sustained release tablets.

BACKGROUND OF THE INVENTION

A zero order release profile for a drug from its controlled release dosage form sometimes is desirable in clinical use. The technology used to formulate zero order release dosage forms is well documented. The entrapment of a drug in a matrix is a common approach to formulate sustained release tablets with a zero order release profile.

It has been reported that depot drug formulations for controlled release of pharmaceutical drugs may be prepared using alginates alone (see U.S. Pat. No. 5,132,295), using combinations of alginates and polyacrylates (see U.S. Pat. No. 5,230,901) and using combinations of alginates and a pH independent hydrocarbon gelling agent, such as, for example, hydroxypropylmethyl cellulose (see U.S. Pat. No. 4,792,452). It is also known that the use of alginates alone for this purpose often presents difficulties in tableting, film coating and storage.

Adding polyacrylates to the alginate formulation overcomes these difficulties to some extent; however, tablets formed using alginates and polyacrylates often have a pH dependent dissolution profile. In a low pH environment, alginates and polyacrylates do not swell and/or dissolve properly. This leads to drug release by a diffusion mechanism through non-viscous capillaries resulting in a different dissolution rate than in a high pH environment. On the other hand, in a high pH environment, alginates swell and become soluble while polyacrylates may or may not do the same. This leads to drug release both by erosion and diffusion at a rate which is different than the low pH release rate.

In formulations which include an alginate and a pH independent gelling polymer such as, for example, hydroxypropylmethyl cellulose, such polymers hydrate at low pH levels to create a viscous gel layer for drug release. At high pH levels, however, tablets become smaller and smaller during drug release due to polymer erosion, and this leads to a reduction in surface area which may affect dissolution rate.

The novelty of the present invention is the provision of a sustained release formulation which reduces, and perhaps eliminates these problems completely. In particular the invention provides a controlled release drug formulation which includes an alginate compound, an enteric polymer, such as polyacrylate, and a gelling polymer, such as, for example, hydroxypropylmethyl cellulose. Such a combination of ingredients facilitates manufacturing procedures and improves drug dissolution profile.

In the formulation in accordance with the present invention, the gelling polymer provides excellent binding and controlled release characteristics thereby facilitating the manufacturing processes. During dissolution, hyroxypropyl methylcellulose hydrates to form a gel layer to control drug release at low pH levels. At high pH levels, enteric polymer increases erosion rate so as to maintain a constant dissolution rate regardless of tablet size. So reduction in tablet size does not reduce release rate. Thus, the formulations of the present invention provide improved drug release profiles compared with the prior art formulations described above.

DETAILED DESCRIPTION OF THE PREFERRED EMBODIMENTS

The present invention provides sustained release tablets formulated with a mixture of a pharmaceutical composition, an alginate, an enteric polymer and a pH independent gelling polymer from which the pharmaceutical composition may be released at a controlled rate. In a particularly preferred form of the invention, the formulation may be used to provide a depot drug form for controlled release of a verapamil containing pharmaceutical composition. However, the formulation is also useful in connection with a variety of other pharmaceutical compositions and the invention should not be considered as being limited by the exact composition and/or nature of the pharmaceutical composition which is released under controlled conditions therefrom.

In a preferred form, the formulation of the invention may contain 1) an alginate component in the form of a water soluble salt of an alginic acid having a viscosity within the range of from about 60 to about 10,000 centipoises, and preferably from about 100 to about 6,000 centipoises, in a 2% by weight water solution at 25° C., as measured by a Brookfield LV viscometer; 2) An enteric polymer composition component, such as a cellulose derivative or a methacrylic acid copolymer (preferably ®Eudragit L/S); and 3) a pH independent gelling polymer component, such as a cellulose derivative or polyethyleneoxide, having a viscosity within the range of from about 10 to about 100,000 centipoises, and preferably from about 50 to about 15,000 centipoises in a 2% by weight water solution at 20° C.

The overall tablet formulation should include the alginate component in an amount so as to establish a weight ratio of alginate:active drug of from about 0.5:1 to about 3:1, and preferably from about 0.7:1 to 1.5:1, in the formulation. Furthermore, the overall tablet formulation should also include the enteric polymer, such as polyacrylate composition component in an amount so as to establish a weight ratio of enteric polymer:active drug of from about 0.1:1 to about 2:1, and preferably from about 0.2:1 to 1:1, in the formulation. Still further, the overall tablet formulation should also include the pH independent gelling polymer component in an amount so as to establish a weight ratio of gelling polymer:active drug of from about 0.03:1 to about 2:1, and preferably from about 0.1:1 to 1:1, in the formulation.

Suitable enteric polyacrylate materials are fully described, for example, in U.S. Pat. No. 5,230,901, the entirety of the disclosure of which is incorporated herein by reference. In this regard, the term polyacrylate is used herein to encompass the polyacrylates, the polymethacrylates and the copolymers of acrylic and methacrylic acid disclosed in the '901 patent. These materials are also described in, for example, Houben-Weyl, Methoden der organischen Chemie, Thieme-Verlag, Stutt, 1961. Products which are commercially available under the name Eudragit® are particularly suitable. Other suitable enteric polymers include, for example, cellulose derivatives such as, cellulose acetate phthalate, cellulose phthalate hydroxypropylmethyl ether, polyvinyl acetate phthalate, etc.

Other ingredients which may be optionally included in the formulation of the invention include 1) one or more binders such as, for example, povidone (polyvinylpyrrolidone), modified starch, low viscosity hydroxypropylmethyl cellulose, etc.; 2) one or more fillers such as, for example, microcrystalline cellulose, lactose, starch, calcium sulfate, etc.; 3) one or more lubricants such as, for example, magnesium stearate, stearic acid, etc.; 4) one or more coating film formers such as, for example, Opadry (a hydroxypropylmethyl cellulose based coating system); and 5) one or more colorants such as, for example, FD&C green dye. The binder materials may be present in an amount up to about 10% by weight of the entire formulation and the lubricant materials may be present in an amount within the range of from about 0.1% to about 5.0% by weight of the entire formulation.

In the specific examples set forth below, three specific embodiments of the invention are exemplified. Theses embodiments have been designated A, B and C.

SPECIFIC EXAMPLES OF THE PREFERRED EMBODIMENTS

| COMPONENT | AMOUNT OF COMPONENT IN EACH EMBODIMENT | | |
|---|---|---|---|
| | A | B | C |
| 1. VERAPAMIL HCL | 240 MG | 120 MG | 240 MG |
| 2. SODIUM ALGINATE | 250 MG | 80 MG | 200 MG |
| 3. HYDROXYPROPYLMETHYL CELLULOSE | 50 MG | 15 MG | — |
| 4. POLYETHYLENEOXIDE | — | — | 60 MG |
| 5. METHACRYLIC ACID COPOLYMER (® Eudragit L/S) | 120 MG | 30 MG | 100 MG |
| 6. POVIDONE | 50 MG | 25 MG | 40 MG |
| 7. MICROCRYSTALLINE CELLULOSE | 60 MG | 80 MG | 80 MG |
| 8. MAGNESIUM STEARATE | 5 MG | 2 MG | 5 MG |

Items 1 through 7 listed above are mixed in a mixer such as a high shear mixer granulator or planetary mixer to obtain homogeneity. The mix is then granulated in water or other suitable granulation fluids and dried in a dryer. The dried granular mass is then milled and then item 8 (a lubricant) is added during milling. The lubricated granular mass is then compressed into tablets using a tablet press. The foregoing steps are conventional steps used in the tablet forming industry.

In the preferred embodiments set forth above, the formulations of the invention have particular utility in the preparation of sustained release tablets of verapamil. However, the invention is not limited to use in connection with this drug only. Tablets containing other drugs requiring sustained release are as well within the intended scope of the invention. For example, it is contemplated that the sustained release formulations of the invention have utility in connection with drugs such as propafenone, barucainide, nesapidil, gallopamil and biperiden. Other suitable pharmaceutical drugs which may require sustained release and which therefore are within the scope of the present invention are listed in U.S. Pat. No. 4,792,452 to Howard et al., the entirety of the disclosure of which is hereby specifically incorporated by reference.

We claim:

1. A controlled release formulation for use in forming a depot drug form, said formulation comprising a pharmaceutical active drug; an amount of an alginate component ranging from 0.5:1 to 3:1 based on the ratio of the said alginate to said active drug; an amount of an enteric polymer effective at pH levels where tablet size change occurs during the dissolution process to prevent changes in drug dissolution rate due to such tablet size change, said amount ranging from 0.1:1 to 2:1 based on the ratio of the said enteric polymer to said active drug; and an amount of a pH independent gelling polymer effective to promote binding and controlled release in the tablet ranging from 0.03:1 to 2:1 based on the ratio of said pH independent gelling polymer to said active drug.

2. A controlled release formulation as set forth in claim 1 wherein said alginate component is a water soluble salt of an alginic acid having a viscosity within the range of from about 60 to about 10,000 centipoises in a 2% by weight water solution at 25° C., as measured by a Brookfield LV viscometer and said pH independent gelling polymer component has a viscosity within the range of from about 10 to about 100,000 centipoises in a 2% by weight water solution at 20° C.

3. A tablet for sustained release of a drug comprising an effective amount of a drug to be released at a controlled rate; and a sustained release formulation comprising three different types of polymers including an alginate component; an amount of an enteric polymer effective at pH levels where tablet size change occurs during the dissolution process to prevent changes in drug release rate due to such tablet size change; and an amount of a pH independent gelling polymer effective to promote binding and controlled release in the tablet, wherein said gelling polymer comprises hydroxypropylmethyl cellulose.

4. A controlled release formulation as set forth in claim 2 comprising 240 parts by weight verapamil as said pharmaceutical compound, 250 parts by weight sodium alginate as said alginate component, 50 parts by weight hydroxypropylmethyl cellulose as said gelling polymer, 30 parts by weight methacrylic acid copolymer as said enteric polymer, 50 parts by weight polyvinylpyrrolidone, 60 parts by weight microcrystalline cellulose, and 5 parts by weight magnesium stearate.

5. A tablet for sustained release of a drug comprising an effective amount of a drug to be released at a controlled rate; and a sustained release formulation comprising three different types of polymers including an alginate component; an amount of an enteric polymer effective at pH levels where tablet size change occurs during the dissolution process to prevent changes in drug release rate due to such tablet size change; and an amount of a pH independent gelling polymer effective to promote binding and controlled release in the tablet, wherein said enteric polymer comprises a cellulose phthalate polymer.

6. A tablet for sustained release of a drug comprising an effective amount of a drug to be released at a controlled rate; an alginate component; an amount of an enteric polymer effective at pH levels where tablet size change occurs during the dissolution process to prevent changes in drug release rate due to such tablet size change; and an amount of a pH independent gelling polymer effective to promote binding and controlled release in the tablet, wherein said alginate component is a water soluble salt of alginic acid having a viscosity within the range of from about 60 to about 10,000 centipoises in a 2% by weight water solution at 25° C., as measured by a Brookfield LV viscometer.

7. A tablet as set forth in claim 6, where said alginate component is a water soluble salt of alginic acid having a viscosity within the range of from about 100 to about 6,000 centipoises in a 2% by weight water solution at 25° C., as measured by a Brookfield LV viscometer.

8. A controlled release formulation as set forth in claim 1 comprising 120 parts by weight verapamil as said pharmaceutical compound, 80 parts by weight sodium alginate as said alginate component, 15 parts by weight hydroxypropylmethyl cellulose as said gelling polymer, 120 parts by weight methacrylic acid copolymer as said enteric polymer, 25 parts by weight polyvinylpyrrolidone, 80 parts by weight microcrystalline cellulose, and 2 parts by weight magnesium stearate.

9. A tablet for sustained release of a drug comprising an effective amount of a drug to be released at a controlled rate; an alginate component; an amount of an enteric polymer effective at pH levels where tablet size change occurs during the dissolution process to prevent changes in drug release rate due to such tablet size change; and an amount of a pH independent gelling polymer effective to promote binding and controlled release in the tablet, wherein said pH independent gelling polymer component is polyethyleneoxide.

10. A tablet for sustained release of a drug comprising an effective amount of a drug to be released at a controlled rate; an alginate component; an amount of an enteric polymer effective at pH levels where tablet size change occurs during the dissolution process to prevent changes in drug release rate due to such tablet size change; and an amount of a pH independent gelling polymer effective to promote binding and controlled release in the tablet, wherein said pH independent gelling polymer component has a viscosity within the range of from about 10 to about 100,000 centipoises in a 2% by weight water solution at 20° C.

11. A tablet as set forth in claim 10, wherein said pH independent gelling polymer component has a viscosity within the range of from about 50 to about 15,000 centipoises in a 2% by weight water solution at 20° C.

12. A controlled release formulation as set forth in claim 1 comprising 240 parts by weight verapamil as said pharmaceutical compound, 200 parts by weight sodium alginate as said alginate component, 60 parts by weight polyethyleneoxide as said gelling polymer, 100 parts by weight methacrylic acid copolymer as said enteric polymer, 40 parts by weight polyvinylpyrrolidone, 80 parts by weight microcrystalline cellulose, and 5 parts by weight magnesium stearate.

13. A controlled release formulation as set forth in claim 1 wherein said active drug is verapamil.

14. A controlled release formulation as set forth in claim 1 wherein said amount of said alginate component ranges from 0.7:1 to 1:1.

15. A controlled release formulation as set forth in claim 1 wherein said amount of said enteric polymer ranges from 0.2:1 to 1:1.

16. A controlled release formulation as set forth in claim 1 wherein said amount of said gelling polymer ranges from 0.1:1 to 1:1.

\* \* \* \* \*